United States Patent [19]

Mano et al.

[11] Patent Number: 5,464,849
[45] Date of Patent: Nov. 7, 1995

[54] N-HYDROXYUREA DERIVATIVES AS ANTIALLERGY AND ANTIINFLAMMATORY AGENTS

[75] Inventors: Takashi Mano; Rodney W. Stevens; Masami Nakane, all of Aichi, Japan

[73] Assignee: Pfizer Inc., New York, N.Y.

[21] Appl. No.: 318,180

[22] Filed: Oct. 5, 1994

Related U.S. Application Data

[63] Continuation of Ser. No. 78,253, filed as PCT/US91/08934, Dec. 5, 1991, abandoned.

[30] Foreign Application Priority Data

Jan. 9, 1991 [JP] Japan .................................. 3-012871

[51] Int. Cl.$^6$ ..................... C07D 263/32; C07D 277/28; A61K 31/425; A61K 31/42
[52] U.S. Cl. ........................... 514/365; 514/374; 548/704; 548/236
[58] Field of Search ..................... 548/204, 236; 514/365, 374

[56] References Cited

U.S. PATENT DOCUMENTS 4,822,809  4/1989  Summers ................................. 514/367

FOREIGN PATENT DOCUMENTS

| | | |
|---|---|---|
| 0292699 | 11/0988 | European Pat. Off. . |
| 0196184 | 10/1986 | European Pat. Off. . |
| 0279263 | 8/1988 | European Pat. Off. . |
| 0388909 | 9/1990 | European Pat. Off. . |
| 8704152 | 7/1987 | WIPO . |

*Primary Examiner*—Robert Gerstl
*Attorney, Agent, or Firm*—Peter C. Richardson; Gregg C. Benson; James T. Jones

[57] ABSTRACT

Compounds of formula I

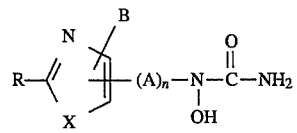

or salts thereof, where R is alkyl, phenyl, phenoxy or substituted phenyl and phenoxy; X is S or O; n is an integer of 1 or 2; A is —CH$_2$— or —CH(CH$_3$)—; and B is hydrogen or methyl, useful as antiallergy and antiinflammatory agents.

12 Claims, No Drawings

N-HYDROXYUREA DERIVATIVES AS ANTIALLERGY AND ANTIINFLAMMATORY AGENTS

This is a continuation of application Ser. No. 08/078,253, filed on Jun. 24, 1993, now abandoned, which is a National filing under 35 U.S. C. 371 based on PCT/US91/08934 filed Dec. 5, 1991.

BACKGROUND OF THE INVENTION

This invention relates to novel N-hydroxyurea derivatives. The compounds of the present invention inhibit the action of lipoxygenase enzyme, and are useful in the treatment or alleviation of inflammatory diseases, allergy and cardiovascular diseases in mammals. This invention also relates to pharmaceutical compositions comprising such compounds.

Arachidonic acid is known to be the biological precursor of several groups of endogenous metabolites, prostaglandins including prostacyclins, thromboxanes and leukotrienes. The first step of the arachidonic acid metabolism is the release of arachidonic acid and related unsaturated fatty acids from membrane phospholipids, via the action of phospholipase. Free fatty acids are then metabolized either by cylooxgenase to produce the prostaglandins and thromboxanes or by lipoxygenase to generate hydroperoxy fatty acids which may be further converted to the leukotrienes. Leukotrienes have been implicated in the pathophysiology of inflammatory diseases, including rheumatoid arthritis, gout, asthma, ischemia reperfusion injury, psoriasis and inflammatory bowel disease. Any drug that inhibits lipoxygenase is expected to provide significant new therapy for both acute and chronic inflammatory conditions.

Recently, several review articles on lipoxygenase inhibitors have been reported. (see H. Masamune and L. S. Melvin, Sr., Annual Reports in Medicinal Chemistry 24 (1989) pp. 71–80 (Academic), B. J. Fitzsimmons and J. Rokach Leukotrienes and Lipoxygenases (1989) pp. 427–502 (Elsevier).

Compounds having structural features similar to those of the present invention are disclosed in European Patent Publication Nos. 279263 A2, and 196184 A2, in U.S. Pat. No. 4,822,809 and Japanese Patent (Kohyo) 502179/1991.

SUMMARY OF THE INVENTION

The compounds of the present invention are of the formula

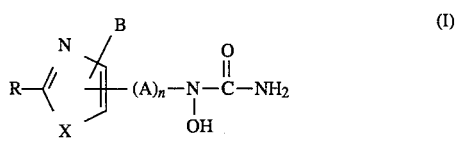

or a pharmaceutically acceptable acid addition salt thereof wherein R is alkyl of one to six carbon atoms, phenyl, substituted phenyl where said substituent is phenyl, phonoxy, methyl, methoxy, fluoro, chloro or trifluoromethyl, phenoxy or substituted phenoxy wherein said substituent is methyl, methoxy, fluoro, chloro or trifluoromethyl; X is S or O; n is an integer of 1 or 2; A is —Ch$_2$— or —CH(Ch$_3$)—; and B is hydrogen or methyl.

Preferred are those compounds where n is 1 and R is phenyl or said substituted phenyl. Especially preferred within this group are N-hydroxy-N-[(2-phenyloxazol)-4-yl)methyl]urea, N-hydroxy-N-[(2-phenylthiazol-4-yl)methyl]urea, N-hydroxy-N-[(2-phenyloxazol-5-yl)methyl]urea, N-hydroxy-N-[(2-phenylthiazol-5-yl)methyl]urea, N-hydroxy-N-[1-{2-(4-phenylphenyl)oxazol-5-yl}ethyl] urea and N-hydroxy-N-[1-{4-methyl-2-(3-phenoxyphenyl)oxazol-5y-1}ethyl]urea.

A second group of preferred compounds are those where R is phenoxy and n is 1. Especially preferred is N-hydroxy-N-[(2-phenoxythiazol-5-yl)methyl]urea.

The present invention also includes a method for treating an allergic or inflammatory condition in a mammal which comprises administering to said mammal an antiallergic or antiiflamatory effective amount of a compound of formula I.

The present invention includes a pharmaceutical composition for the treatment of allergic or inflammatory conditions which comprises an antiallergic or antiinflammatory effective amount of a compound of formula I or a pharmaceutically acceptable salt together with a pharmaceutically acceptable carrier.

Finally, the present invention includes a process for preparing a compound of formula I where R, X, A, B and D are as previously indicated which comprises reacting a compound of the formula

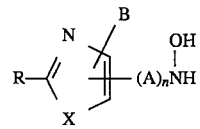

with an alkali metal cyanate or a trialkylsilylisocyanate having three to nine carbon atoms in a reaction-inert solvent until the reaction is substantially complete.

The term "pharmaceutically-acceptable salt" used herein means a non-toxic cation, including those of alkaline earth metals such as sodium, lithium, calcium and magnesium, and organic cation bases of ammoniums and amines, or non-toxic phosphate or acid phosphate, acetate, citrate, fumarate, gluconate, lactate, maleate, succinate tartrate, methanesulfonate, benzenesulfonate, hydrogen halides, toluenesulfonate, and formate salts thereof.

DETAILED DESCRIPTION OF THE INVENTION

The compounds of the instant invention are prepared by reacting an N-hydroxy amine with a trialkylsilylisocyanate in a reaction-inert solvent, such as tetrahydrofuran, at room temperature. Equimolar amounts of the reagents can be employed with a slight excess of the isocyanate.

The reaction time is dependent on the reactivity of the reactants and the reaction temperature. At room temperature the reaction is usually complete in several (2–4) hours.

The product can be isolated by removing the solvent in vacuo or, if the solvent is water miscible, the reaction mixture can be diluted with water and the product filtered or extracted. The isolated product can be purified by conventional means.

As a modification of this procedure the compounds of the present invention can also be prepared by reacting the hydroxyl amine as an acid addition salt with an equimolar amount of an alkali metal cyanate, such as potassium cyanate, in water. As the reaction proceeds the product precipitates from the reaction. When the reaction is complete (20–45 min. at 0°–25° C.) the product is filtered _ and purified.

The starting reagents needed to synthesize the compounds of the present invention are either readily available or can be prepared by reaction sequences known to those skilled in the art.

The pharmaceutically-acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent; or, in the case of a nontoxic acid salt, an appropriate mineral or organic acid in either aqueous solution or suitable organic solvent. The respective salt can then be obtained by precipitation or by evaporation of the solvent.

The compounds of this invention inhibit the activity of the lipoxygenase enzyme. This inhibition has been demonstrated by an assay using rat periotoneal cavity resident cells which determines the effect of said compounds on the metabolism of arachidonic acid.

All of the compounds were tested according to the methods described in Jap. J. Inflammation 7:145–150, 1987, "Synthesis of leukotrienes by peritoneal macrophages" and those were shown to possess the efficacy of inhibiting lipoxygenase activity.

In this test some preferred compounds indicate low IC50 values, in the range of 0.01 to 30 μM, with respect to lipoxygenase inhibition.

The ability of the compounds of the present invention to inhibit lipoxygenase enzyme make them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor, e.g., allergic bronchial asthma, skin disorders, rheumatoid arthritis, osteoarthritis and thrombosis.

Thus, the compounds of formula I and their pharmaceutically-acceptable salts are of particular use in the treatment or alleviation of inflammatory diseases, allergy and cardiovascular diseases in a human subject.

For treatment of the various conditions described above, the compounds and their pharmaceutically-acceptable salts can be administered to a human subject either alone, or, preferably, in the combination with pharmaceutically-acceptable carriers of diluents in a pharmaceutical composition, according to standard pharmaceutical practice. A compound can be administered by a variety of conventional routes of administration including oral, parenteral and by inhalation. When the compound is administered orally, the dose range will be from about 0.1 to 20 mg/kg per day in single or divided doses. If parenteral administration is desired, then an effective dose will be from 0.1 to 1.0 mg/kg body weight of the subject to be treated per day. In some instances it may be necessary to use dosages outside these limits, since dosage will necessarily vary according to the age, weight and response of the individual patient as well as the severity of the patients symptoms and the potency of the particular compound being administered.

For oral administration, the compounds of the invention and their pharmaceutically-acceptable salts can be administered, for example, in the form of tablets, powders, lozenges, syrups or capsules, or as an aqueous solution or suspension. In the case of tablets for oral use, carriers which are commonly used include lactose and corn starch. Further, lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solution of the active ingredient are usually prepared, and the pH of the solutions should be suitably adjusted and buffered. For intravenous use, the total concentration of solute should be controlled to make the preparation isotonic.

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multipier; br, broad.

EXAMPLE 1

N-Hydroxy-N-[(2-phenyloxazol-4-yl)methyl]urea 1A. 2-Phenyloxazole-4-carboxaldehyde oxime To a solution of 2-phenyloxazole-4-carboxaldehyde (2.18 g, 12.5 mmol) in pyridine (25 ml) was added hydroxylamine hydrochloride (0.96 g, 13.8 mmol) under stirring at room temperature. After 1 hour the mixture was poured into water (200 ml) and the resulting solids were collected, washed with water and dried under vacuum. 2.02 g (10.8 mmol) of the titled compound was obtained: mp 145°– 147° C.; IR (KBr) 3195, 3075, 3035, 2850, 1646, 1555, 1486, 1445, 1431 cm$^{-1}$; 1H NMR (270 MHz, CDCl$_3$) d 8.87 (brs,1H), 8.51 (s,1H), 8.09–8.05 (m,2H), 7.68 (sy,1H), 7.52–7.47 (m,3H).

1B. N-Hydroxy-N-[(2-phenyloxazol-4-yl)methyl] amine

To a solution of oxime$^{1A}$ (1.71 g, 9 mmol) and borane-pyridine complex (1.67 g, 18 mmol) was slowly added a mixture of aqueous conc HCl (7.5 ml) and ethanol (7.5 ml) under stirring at 0° C. After the addition was complete, the cooling bath was removed and the mixture was stirred at room temperature for 1 h and then neutralized with water (100 ml) and extracted with ethyl acetate (200 ml+ 2×100 ml). The combined organic layers were washed with brine, dried over MgSO$_4$ and evaporated to dryness. The resultant oil solidified on standing overnight. Washing the solids with cold toluene (2×3 ml) gave 1.32 g (6.9 mmol) of the titled compound (mp 59°–61° C.). Concentration of the washed gave another 0.22 g (1.2 mmol) of the titled compound (mp 70°–71° C.): IR (KBr) 3250, 3120, 2910, 1605, 1593, 1548, 1478 cm$^{-1}$; 1H NMR (270 MHz, CDCl$_3$) 8.00 (s,1H), 8.00–7.94 (m,2H), 7.56–7.51 (m,3H), 7.42 (s,1H), 5.95 (brs, 1H), 3.84 (s,2H).

1C. N-Hydroxy-N-[(2-phenyloxazol-4-yl) methyl] urea

A solution of hydroxylamine$^{1B}$ (1.33 g, 7 mmol) and trimethylsilylisocyanate (90%, 1.12 g, 8.75 mmol) in THF (70 ml) was stirred at room temperature for 2 hours. After insoluble material was filtered off, the solvent was evaporated off. Recrystallization of the crude product twice from 2-propanol gave 0.84 g (3.6 mmol) of the titled compound: mp 162°–163° C. (decomp); IR (KBr) 3435, 3280, 3200, 2970, 2895, 1655, 1595, 1550, 1506, 1481, 1444, 1427, 1406 cm$^{-1}$; 1H NMR (270 MHz, DMSO-d$_6$) d 9.41 (s, 1H), 8.01 (s, 1H), 7.99–7.94 (m,2H), 7.55–7.51 (m, 3H), 6.45 (brs, 2H), 4.47 (s,2H).

Anal. Calcd for $C_{11}H_{11}N_3O_3$: C, 56.64; H, 4.75; N, 18.01. Found: C, 57.00; H, 4.89; N, 17.61.

EXAMPLES 2–4

Employing the procedures of Example 1 and starting with the requisite starting materials, the following compounds were prepared:

N-hydroxy-N-[(2-phenylthiazol-4-yl)methyl] urea, m.p. 133.5°–134° C. NMR(270 MHz, CDCl$_3$) 8.82(brs, 1H), 7.88–7.84 (m, 2H), 7.46–7.43(m, 3H), 7.12(s, 1H), 5.35(brs, 2H) and 4.86(s, 2H).

N-hydroxy-N-[(2-phenoxythiazol-5-yl)methyl] urea, m.p. 174°–175° C., NMR (270 MHz, DMSO-d$_6$) 9.53(s, 1H), 7.52–7.45(m, 2H), 7.35–7.28(m, 3H), 7.15(s, 2H), 6.46(brs, 2H) and 4.52 (s, 2H).

N-hydroxy-N-[(2-phenylthiazol-5-yl) methyl] urea, m. p 190.5°–191° C. NMR(270 MHz, DMSO-d$_6$) 9.59(s,1H), −7.93–7.88(m, 2H), 7.76(s, 1H), 7.52–7.47(m, 3H), 6:49(brs, 2H) and 4.71(s, 2H).

EXAMPLE 5

N-Hydroxy-N-[(2-phenyloxazol-5-yl)methy] urea 5A. 2-Phenyloxazole-5-Carboxaldehyde oxime This compound was obtained as a stereoisomeric mixture (64:36) from 2-phenyloxazole-5-carboxaldehyde according to previously used procedure. Yield was 81%: 1H NMR (270 MHz, CDCl$_3$) δ8.15–8.08 (m, 2H), 8.12 (s, 0.36H), 8.04 (s, 0.64H), 7.67 (s, 0.64H), 7.53–7.45 (m,3H), 7.43 (s, 0.36H).

5B. N-Hydroxy-N-[(2-phenyloxazol-5-yl)methyl] amine

To a stirred solution of the oxime (2.82 g, 15 mmol) and borane-pyridine complex (2.09 g, 22.5 mmol) in ethanol (60 ml) at 0° C. was slowly added a mixture of concentrated aqueous hydrochloric acid (10 ml) and ethanol (10 ml). After addition was complete, the cooling bath was removed and the mixture was stirred at room temperature for 1.5 h and then neutralized with 2N aqueous sodium hydroxide. Ethanol was removed under a reduced pressure, and the residue was extracted with ethyl acetate (100 ml+2×50 ml). The combined extracts were washed with saturated aqueous sodium bicarbonate (50 ml) and brine (50 ml), dried over MgSO$_4$ and evaporated to dryness. The resultant oil was treated with 10% hydrogen chloride methanol solution and evaporation of volatiles yielded 2.75 g of crude N-hydroxy-N-[(2-phenyloxazol-5-yl)methyl] amine hydrochloride salt.

5C. N-hydroxy-N-[(2-phenyloxazol-5-yl)methyl] urea

The hydrochloride salt of Example 5B was treated with water (60 ml), and after cooling insolubles were removed by filtration. To the stirred filtrate cooled to 0° C. was added a solution of potassium cyanate (1.22 g, 15 mmol) in water (10 ml) and the resultant mixture was stirred at 0° C. for 20 min. The resulting white precipitate was collected by filtration, washed with water, and dried under a vacuum to afford 1.21 g of the crude hydroxyurea. Recrystallization from 25% ethanol in methanol (ca. 100 ml) gave 0.69 g of the first crop. The second crop (0.18 g) was also obtained by concentrating the mother liquid. The combined two crops were dissolved in minimal hot methanol (100 ml), and the mixture was filtered while hot, concentrated to ca. 20 ml under a reduced pressure, and cooled in a refrigerator for 2 h. Product was collected by filtration, washed with ethanol (3×3 ml), and dried under vacuum at 60° C. overnight to give the titled compound (0.68 g, 19% from the oximes[5A]): mp 190–191° C. (decomp.); IR (KBr) 3485, 3185, 1667, 1652, 1568 cm$^{-1}$; 1H NMR (270 MHz, DMSO-d$_6$) δ9.55 (s, 1H), 7.98–7.93 (m, 2H), 7.56–7.50 (m, 3H), 7.18 (s, 1H), 6.55 (br s, 2H), 4.64 (s, 2H); Anal. Calcd for $C_{11}H_{11}N_3O_3$: C, 56.64; H, 4.75; N, 18.01. Found: C, 56.81; H, 4.51; N, 18.12.

EXAMPLE 6

N-Hydroxy-N-[1-{5-methyl-2-(3-phenoxyphenyl)oxazol-5-yl}ethyl]urea 6A. 5-Acetyl-4-methyl-2-(3-phenoxyphenyl)oxazole A mixture of 3-phenoxybenzamide (2.13 g, 10 mmol), 3-phenoxybenzoic acid (4.28 g, 20 mmol), and 3-chloropenta-2,4-dione (0.44 g, 3.3 mmol) was heated to 180° C. under stirring for 23 h. The hot mixture was poured into 1N aqueous sodium hydroxide (100 ml), and extracted with diethyl ether (100+2×50 ml). The combined organic phases were washed with saturated aqueous sodium bicarbonate (50 ml) and brine (50 ml), dried over magnesium sulfate, and evaporated to dryness. Purification by silica gel column chromatography (135 g, 16.7% ethyl acetate in n-hexane) afforded the titled compound as solids in 94% yield: 1H NMR (CDCl$_3$) δ7.88–7.83 (1H, m), 7.77–7.53 (1H, m), 7.49–7.34 (3H, m), 7.18–7.12 (2H, m), 7.07–7.00 (2H, m), 2.55 (3H, s), 2.54 (3H, s).

6B. 5-Acetyl-4-methyl-2-(3-phenoxyphenyl)oxazole oxime

To a solution of 5-acetyl-4-methyl-2-(3-phenoxyphenyl)-oxazole[6A](0.30 g, 1.0 mmol) in pyridine (2.5 ml) was added hydroxylamine hydrochloride (0.69 g, 10.0 mmol) and the mixture was stirred at room temperature for 20 min. The reaction mixture was diluted with water (15 ml) and extracted with diethyl ether (2×15 ml). The combined extracts were washed with water (3×10 ml) and brine (10 ml), and dried over magnesium sulfate. Evaporation of volatiles yielded the titled compound in quantitative yield. This product was used for the next step without further purification: 1H NMR (CDCl$_3$) δ8.65– 8.62 (1H, m), 8.21 (brs, 1H), 7.81–7.69 (m, 2H), 7.45–7.28 (3H, m), 7.16–7.01 (3H, m), 2.41 (3H, s), 2.29 (3H, s).

6C. N-Hydroxy-N-[1-{5-methyl-2-(3-phenoxyphenyl)oxazól-5-yl}ethyl]amine

5-Acetyl-4-methyl-2-(3-phenoxyphenyl) oxazole oxime[6B] (0.31 g, 1 mmol) was dissolved in mixture of ethanol (10 ml) and pyridine (1 ml) cooled to 0° C. Borane pyridine complex (0.28 g, 3.0 mmol) was added via syringe under a nitrogen atmosphere followed 30 min. later at room temperature by a mixture of concentrated aqueous hydrochloric acid (2.5 ml) and ethanol (2.5 ml). After 1 h the reaction mixture was neutralized with 2N aqueous sodium hydroxide, and extracted with ethyl acetate (30 ml). The extract was washed with water (10 ml) and brine (10 ml), dried over magnesium sulfate, and evaporated. The resulting solids were purified by silica gel column chromatography (30 g; 50–67% ethyl acetate in n-hexane). Yield was 13%: 1H NMR (CDCl$_3$) δ7.78–7.33 (1H, m), 7.68–7.66 (1H, m), 7.42–7.31 (3H, m), 7.15–7.00 (4H, m), 4.30 (1H, q J=6.96 Hz), 2.23 (3H, s), 1.44 (3H, d, J=6.96 Hz).

6D. N-Hydroxy-N-[1-{5-methyl-2-(3-phenoxyphenyl)oxazol-5-yl}ethyl]urea

To a solution of N-hydroxy-N-[1-{5-methyl-2-(3-phenoxyphenyl)oxazol-5-yl}ethyl]amine[6C] (35mg, 0.11 mmol) in tetrahydrofuran (3 ml) at room temperature was added trimethylsilylisocyanate (95%, 19 mg, 0.16 mmol). After 1.5 h methanol (1 ml) was added and the mixture was stirred for 10 min. Volatiles were evaporated off, and the residue was mostly dissolved into hot 40% ethyl acetate in diisopropyl ether (10 ml), filtered while hot, concentrate to about a half volume, and cooled in a ice-water bath. Collection of solids by filtration followed by washing with diisopropyl ether (3 ml) yielded the titled compound in 57% yield: 1H NMR (CDCl$_3$) δ9.22 (1H, brs), 7.68–7.44 (5H, m), 7.32–7.07 (4H, m), 6.41 (1H, m), 5.42 (1H, q, J=6.96 Hz), 2.13 (3H, s), 1.44 (3H, d, J=6.96 Hz).

EXAMPLE 7

N-Hydroxy-N-[1-{2-(4-phenylphenyl)oxazol-5-yl}ethyl] urea 7A. 2-(4-Phenylphenyl)oxazole A mixture of p-phenylbenzamide (20.11 g, 0.10 mmol), vinylenecarbonate (8.61 g, 0.10 mmol), and polyphosphoric acid (90 g) was heated to ca. 165° C. with occasional shaking for 1.5 h. The hot reaction mixture was poured into ice (100 g) and neutralized with 20% aqueous sodium hydroxide. The resulting solids were collected by filtration, washed with water (4×20 ml), and dried under vacuum at room temperature. Sublimation of the crude product afforded the titled compound in 28% yield (150°–153° C./4–6 mmHg): 1H NMR (CDCl$_3$) δ8.12 (2H, d, J=8.79 Hz), 7.73 (1H, d, J=0.73 Hz), 7.70 (2H, d, J=8.79 Hz), 7.66–7.61 (2H, m), 7.50–7.34 (3H, m), 7.27 (1H, d, J=0.73 Hz).

7B. 2-(4-phenylphenyl)oxazole-5-carboxaldehyde

To a solution of 2-(4-phenylphenyl)oxazole 7A (5.53 g, 25 mmol) in DMF (30 ml) was slowly added phosphorous oxychloride (10.73 g, 70 mmol) at −5°–0° C. during 20 min. The reaction mixture was stirred at room temperature for 15 min. and then at 95° C. for 20 h. After cooling, the reaction mixture was poured into ice (100 g), neutralized with 20% aqueous sodium hydroxide, and extracted with ethyl acetate (200+2×100 ml). The combined extracts were washed with water (3×50 ml) and brine (50 ml), and dried over magnesium sulfate. Evaporation of volatiles gave yellow brown solids (6.34 g). Silica gel column chromatography (300 g; 12.5–25% ethyl acetate in n-hexane) yielded the titled compound as solids in 46% yield: IR (KBr) v(C═O) 1680 cm$^{-1}$; 1H NMR (CDCl$_3$) δ9.84 (1H, s) , 8.26 (2H, d, J=8.79 Hz), 7.97 (1H, s), 7.75 (2H, d, J=8.79 Hz), 7.68–7.64 (m, 2H), 7.52–7.38 (m, 3H).

7C. 1-Hydroxy-1-{2-(4-phenylphenyl]oxazole}ethane

To a solution of 2-(4-phenylphenyl)oxazole-5 -carboxaldehyde 7B (2.74 g, 11 mmol) in tetrahydrofuran (100 ml) at 0° C. under a nitrogen atmosphere was slowly added a 0.96M solution of methylmagnesium bromide in tetrahydrofuran (13.8 ml, 13.2 mmol) during 10 min. After stirring at 0° C. for 1.5 h, the reaction was quenched by adding saturated aqueous ammonium chloride (50 ml). To the resulting mixture was added water (50 ml) and the layers separated. The aqueous layer was extracted with diethyl ether (50 ml), and the combined organic layers washed with brine (50 ml), dried over magnesium sulfate, and evaporated to dryness. The resulting solids were recrystallized from ethyl acetate to afforded the titled compound in 83% yield: mp 140–141° C.; IR (KBr) v(OH) 3250 cm$^{-1}$; 1H NMR (CDCl$_3$) δ8.10 (2H, d, J=8.79 Hz), 7.69 (2H, d, J=8.79 Hz), 7.66–7.61 (2H, m), 7.50–7.35 (3H, m), 7.07 (1H, d, J=0.73 Hz), 5.04 (1H, dq, J=0.73, 6.60 Hz), 1.98 (1H, brs), 1.65 (1H, d, J=6.60 Hz).

7D. N,O-Di-tert-butoxycarbonyl-N-[1-{2-(4 -phenylphenyl)oxazol}ethyl]-hydroxylamine To a stirred solution of 1-hydroxy-1-{2-(4 -[penylphenyl)oxazole}ethane 7C (66 mg, 0.25 mmol), N,O-di-tert-butoxycarbonylhydroxylamine (70mg, 0.3 mmol), and triphenylphosphine (79 mg, 0.3 mmol) in toluene (2.5 ml) at room temperature under a nitrogen atmosphere was added diethylazodicarboxylate (52 mg, 0.3 mmol) via syringe. The resulting mixture was stirred at room temperature overnight. The reaction mixture was directly purified by silica gel column chromatography (30 g; 25% ethyl acetate in n-hexane) to afford the desired compound in 54% yield: 1H NMR (CDCl$_3$) d 8.07 (br, 2H), 7.70–7.62 (4H, m), 7.50– 7.34 (3H, m), 7.08 (br, 1H), 5.59–5.55 (1H, m), 1.64 (3H, d, J=6.60 Hz), 1.53 (18H, s).

7E. N-Hydroxyl-N-[1-{2-(4-phenylphenyl)oxazol-5 -yl}ethyl]urea

A solution of N,O-tert-butoxycarbonyl-N-[1-{2-(4 -phenylphenyl)oxazole}ethyl]hydroxylamine 7D (93 mg, 0.22 mmol) in dichloromethane (6 ml) was treated with trifuloroacetic acid (0.4 ml) at room temperature. After evaporation of volatiles the residue was covered with saturated aqueous sodium bicarbonate (30 ml) and extracted with ethyl acetate (30±2×10 ml). The combined extracts were washed with saturated aqueous sodium bicarbonate (10 ml) and brine (10 ml), dried over magnesium sulfate, and evaporated to give 50mg of N-{1-{-(4 -phenylphenyl)oxazole}ethyl}hydroxylamine.

To a solution of the crude hydroxylamine obtained in tetrahydrofuran (2.5 ml) at room temperature was added trimethylsilylisocyanate (95%, 33mg, 0.27 mmol). After stirring 30 min. methanol (1 ml) was added and the resulting mixture was stirred for 10 min. Evaporation of volatiles afforded a crude product, which was recrystallized from 25% ethyl acetate in ethanol. Yield was 50%: 1H NMR (CDCl$_3$) δ9.24 (brs, 1H), 8.02 (2H, d, J=8.79 Hz), 7.83 (2H, d, J=8.79 Hz), 7.77–7.73 (m, 2H), 7.54–7.41 (m, 3H), 7.17 (1H, d, J=0.73 Hz), 6.55 (brs, 1H), 5.60 (dq, 1H, J=0.73, 6.60 Hz), 1.54 (3H, d, J=6.60 Hz).

We claim:

1. A compound of the formula

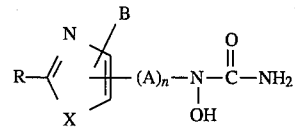

of a pharmaceutically acceptable acid addition salt thereof wherein R is alkyl having one to six carbon atoms, phenyl, substituted phenyl wherein said substituent is phenyl, phenoxy, methyl, methoxy, fluoro, chloro or trifluoromethyl; phenoxy or substituted phenoxy wherein said substituent is methyl, methoxy, fluoro, chloro or trifluoromethyl; X is S or O; n is an inter of 1 or 2; A is —CH$_2$ or —CH(CH$_3$)— and B is hydrogen or methyl.

2. A compound of claim 1, wherein n is 1 and R is phenyl or said substituted phenyl.

3. The compound of claim 2, N-hydroxy-N-[(2-phenyloxazol-4 -yl)methyl]urea.

4. The compound of claim 2, N-hydroxy-N-[(2 -phenylthiazol-4-yl)methyl]urea.

5. The compound of claim 2, N-hydroxy-N-[(2 -phenyloxazol-5-yl)methyl]urea.

6. The compound of claim 2, N-hydroxy-N-[(2 -phenylthiazol-5-yl)methyl]urea.

7. The compound of claim 2, N-hydroxy-N-[1-{4-methyl-2 -(3-phenoxyphenyl)oxazol-5-yl}ethyl]urea.

8. The compound of claim 2, N-hydroxy-N-[1-{2-(4 -phenylphenyl)oxazol-5-yl}ethyl]urea.

9. A compound of claim 1, wherein R is phenoxy and n is 1.

10. The compound of claim 9, N-hydroxy-[(2-phenoxythiazol-5-yl)methyl]urea.

11. A method for treating an allergic or inflammatory condition in a mammal which comprises administering to said mammal an antiallergy or antiinflammatory effective amount of a compound according to claim 1.

12. A pharmaceutical composition for the treatment of allergic or inflammatory conditions in a mammal, said composition comprising an effective amount of a compound according to claim 1 with a pharmaceutically acceptable carrier.

* * * * *